United States Patent [19]
Frola et al.

[11] Patent Number: 5,124,659
[45] Date of Patent: Jun. 23, 1992

[54] MEASUREMENT OF PH AND SPECIFIC ION CONCENTRATION

[75] Inventors: Frank R. Frola, North Huntington; John T. Schneider, Washington Township, Westmoreland County, both of Pa.

[73] Assignee: Fisher Scientific Company, Pittsburgh, Pa.

[21] Appl. No.: 485,329

[22] Filed: Feb. 20, 1990

Related U.S. Application Data

[63] Continuation-in-part of Ser. No. 313,070, Feb. 21, 1989, Pat. No. 4,912,417.

[51] Int. Cl.$^5$ .............................. G01R 35/00
[52] U.S. Cl. ................... 324/438; 324/601; 324/722; 324/74; 324/130; 73/1 R
[58] Field of Search ............. 324/438, 439, 601, 691, 324/722, 525, 527, 74, 130; 73/1 R, 1 G

[56] References Cited

U.S. PATENT DOCUMENTS

| | | | |
|---|---|---|---|
| 4,752,740 | 6/1988 | Steininger | 324/439 X |
| 4,799,174 | 1/1989 | Kramer et al. | 324/601 X |
| 4,841,229 | 6/1989 | Eccleston | 324/601 |
| 4,912,417 | 3/1990 | Gibboney et al. | 324/438 |
| 4,940,946 | 7/1990 | Nazaryan | 324/439 X |

Primary Examiner—Kenneth A. Wieder
Attorney, Agent, or Firm—Alan M. Doernberg

[57] ABSTRACT

A microprocessor-controlled pH and ion concentration meter is disclosed with improved testing procedures. The meter can be tested for excessive internal bias current by measuring the potential (V1) when the meter is connected to a circuit a known voltage (E1) of low impedance and the potential (V2) when the meter is connected to a circuit of the same voltage source (E1) but of known high impedance and having the meter compare (V2−V1) to a preset limit value. The meter can be tested for low internal impedance by further measuring the potential (V4) when the meter is connected to a circuit of a second external voltage (E2) and the known high impedance (R1). The meter then calculates:

$$(V4 - V2)$$

and compares that value to preset limits based upon E1, E2 and R1. Such limits can be derived as $(Z_o)(E2-E1)/(R_1+Z_o)$ where $Z_o$ is the minimum acceptable internal impedance.

5 Claims, 6 Drawing Sheets

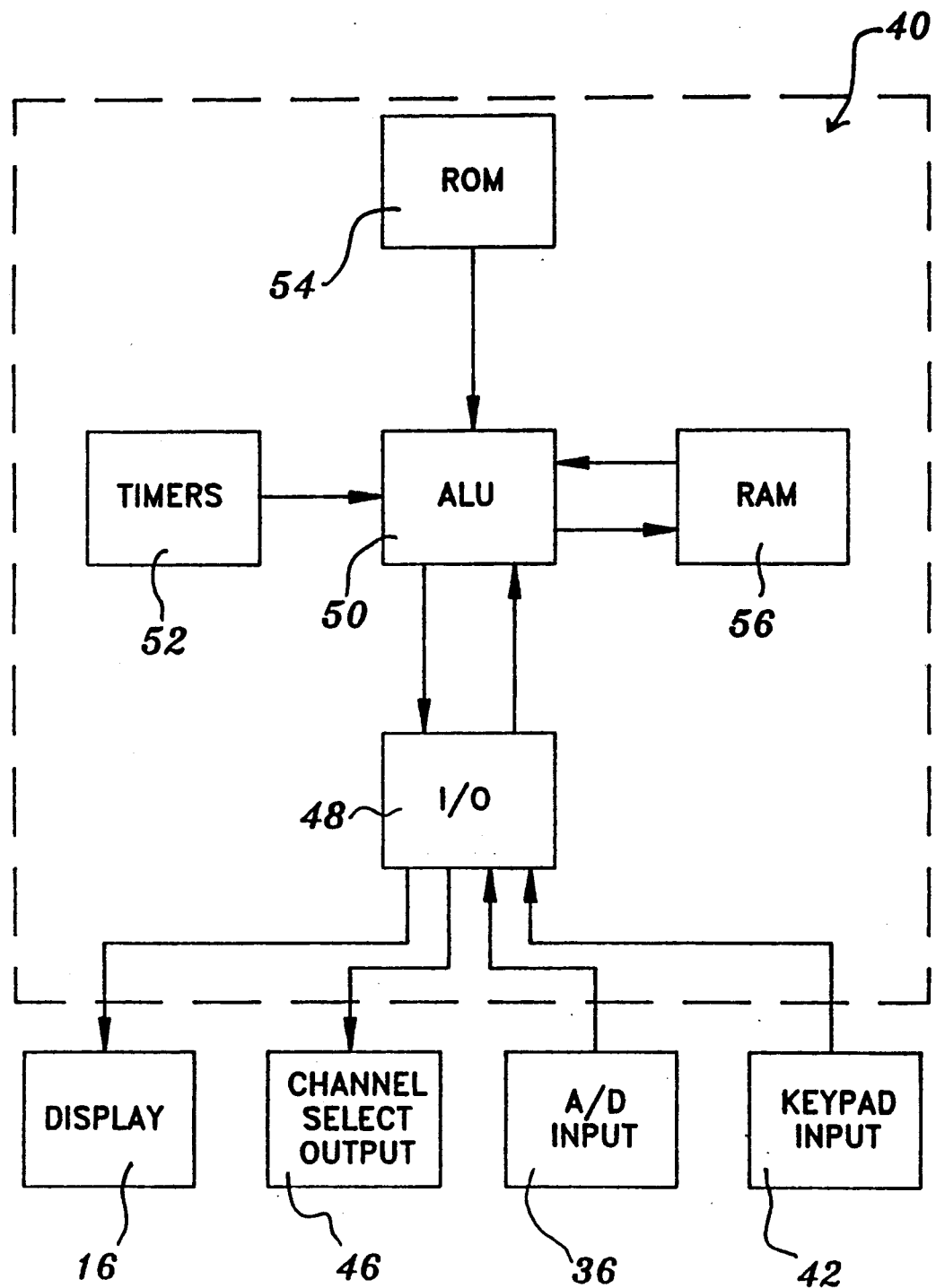

MEASUREMENT OF PH AND SPECIFIC ION CONCENTRATION

This is a continuation-in-part of U.S. Ser. No. 313,070 of Gibboney et al, filed Feb. 21, 1989, copending and commonly-assigned, now U.S. Pat. No. 4,912,417.

The present invention relates to measuring pH and specific ion concentrations potentiometrically, and especially to meters for use in combination with electrodes for such measurement.

Electrodes for measuring hydronium (pH) and other ions such as alkali metal, ammonium or alkaline earth metal cations or halide or sulfide anions are well known. Typically, the electrodes are first connected electrically to a meter which serves to measure the potential difference between the indicating electrode and the reference electrode. The indicating and reference electrodes, separately or in combination form, are then immersed in the unknown solution. The meter converts the measured electrical potential to a calculated and displayed value referred to as pX (pH in the case of hydronium cations). For ions other than hydronium, a concentration value (in units such as ppm) is calculated from the exponent pX and displayed.

Various problems are encountered in the testing and operation of the meter. These problems include: (1) ensuring that the input bias current (of the input operational amplifier of the meter) is sufficiently low to have no significant effect upon the measured electrical potential, (2) ensuring that the internal impedance of the meter is sufficiently high to have no significant effect upon the measured electrical potential, and (3) establishing when the measured electrical potential (whether from a test circuit or an electrode input) is acceptably stable. Each of these operations has often led to excessive manual operations by the meter manufacturer or by the user.

In determining whether the internally-generated voltage of the meter is a cause for excessive error, either at the time of manufacture or after use, it has been possible to connect the meter to a test circuit having additional resistance (generally much larger than the resistance of the electrode in use), a difference in measured voltage can be obtained. Traditionally, this difference has been converted by external calculation to a value for bias current. This bias current value can be used to estimate the pX or pH error that results from the high impedance of the measuring electrode. An example of such a computation is shown below:

$$pH_{error} = Slope_{(units/volts)} * R_{electrode} * I_{bias}$$

and for a typical electrode at 25 deg C.

$$pH_{error} = 17 * 10^8 * I_{bias}$$

where $I_{bias}$ is computed as:

$$I_{bias} = \frac{V_{no\ resistor} - V_{with\ 5G\ resistor}}{5 * 10^9}$$

The difficulty in this procedure is that it requires both multiple manual manipulations and a calculation which, even if automated, must employ a calculating device external to the meter.

In the case of determining the internal impedance of the meter four different values of measured voltage are obtained with the meter in different test circuits: with two different applied voltages in the test circuit and two different resistances in the test circuit. All four values of measured voltage are then written down and an internal impedance is then calculated based upon the two different applied voltage values, the two different external resistance values and the four different values of measured voltage, using for example, a calculator.

Finally, whether connected to electrodes or to any external circuit for testing, the meter measures an input voltage which varies over time. This variation is steep initially, typically assymptotically approaching a final value within 10-30 seconds for pH electrodes. This interval is often much longer for other electrode types, e.g., gas sensors such as carbon dioxide or ammonia electrodes. Some meters are commercially designed to wait a fixed period before taking a measurement of voltage from which a standardization value is taken or a pX is calculated. Others take a running average of values at fixed intervals and display that average. Meters with multiple resolution settings have been employed which wait different fixed periods of time after first reading depending upon the resolution selected (e.g., 4 seconds for a resolution of 0.1 pH units, 8 seconds for a resolution of 0.01 pH units and 16 seconds for a resolution of 0.001 pH units). Any such method based upon time alone fails to recognize differences in basic design, sample history and environment among electrode pairs or differences between test circuits and electrode pair circuits. Any such method which compares the running average to latest value with a fixed criterion ignores the relevance of resolution: it may wait too long in low resolution settings and measure too soon for high resolution settings.

The field of meters for pH and pX electrodes has also undergone trends towards minaturization, increased offering of automated features and incorporation of more modern electronic components.

BRIEF DESCRIPTION OF THE INVENTION

The present invention provides meter devices and methods which accomplish one or more of the testing, calibration and measuring functions described above in an improved fashion. The improvements minimize manual operations, reduce time and expertise required for meter testing during production and reduce user time spent calibrating the system in use.

In one form of the invention (which form is claimed in parent U.S. Ser. No. 313,070, now U.S. Pat. No. 4,912,417), the present invention provides a method for testing a pH or pX meter for excessive internal bias current which comprises the steps:

a) connecting the electrode inputs of the meter to an external circuit having a known voltage of value E1 and a low external resistance and storing the measured voltage V1, b) connecting the electrode inputs of the meter to an external circuit having the known voltage E1 and a large known resistance R1 and storing the measured voltage V2, c) having the meter calculate the value of the difference between V1 and V2, d) having the meter compare the calculated difference to a permitted range which is preset in the meter and is based upon fixed values of E1 and R1, and e) if the difference between V1 and V2 is outside the preset limits, having the meter display an error message indicating that the meter is out of specification.

In a second form, the invention provides a method for testing a pH or pX meter for low internal impedance which comprises the steps:

a) connecting the electrode inputs of the meter to an external circuit having a known voltage E1 and a large known external resistance R1 and storing the measured voltage V2, b) connecting the electrode inputs of the meter to an external circuit having a known voltage of value E2 and the large known external resistance R1 and storing the measured voltage V4, c) having the meter calculate the value:

$$(V_4 - V_2)$$

and compare that calculated value to a permitted range which is preset in the meter and is based upon fixed values of E1, E2 and R1, and d) if that calculated value is outside preset limits, having the meter display an error message indicating that the meter is out of specification for internal impedance.

It is preferred, but not required, that the meter measure the $V_1$ value as described in the first form and the $V_4$ as described in the second form and the $V_2$ value as described in both forms of the invention as part of an overall evaluation protocol so that the meter can be evaluated for both internal bias current and internal impedance. It is also preferred, but not required, that the meter be put in a test circuit having the external voltage E2 and the low external resistance of step (a) of the first method in order to obtain a measured voltage value $V_3$. The difference between $V_3$ and $V_4$ can be used to verify bias current at the low external resistance just as $V_1$ and $V_2$ had been used to verify bias current at the high external resistance.

In each form of the invention, it is preferred that each measuring step performed by the meter include steps:

1) taking and storing measured voltage values at fixed intervals (e.g., every one second), 2) calculating the average of the stored set of values, 3) as each additional value is stored beyond a fixed number (e.g., 5), discarding the oldest value and calculating a new average of the set of values, 4) comparing each calculated average to the most recent value stored and determining a difference therebetween, and 5) when the difference is an amount greater than an amount set as the resolution of the meter (or otherwise set as a threshold) for a fixed time period (e.g., 5 seconds), then repeating (3), (4) and (5), and 6) once the difference is an amount no more than an amount set as the resolution of the meter (or as otherwise set as a threshold), then storing and/or displaying the latest value or the running average.

BRIEF DESCRIPTION OF THE DRAWING

FIG. 2 is a schematic view of the major functional elements of the microprocessor 40 shown in FIG. 1B and its functional connection to other components of the meter;

DETAILED DESCRIPTION OF THE INVENTION

Various aspects of the invention will be illustrated and explained with reference to the single embodiment of a meter shown in the various Figures at various stages of testing, standardization and use.

DESCRIPTION OF A PREFERRED EMBODIMENT

Figure 1A:
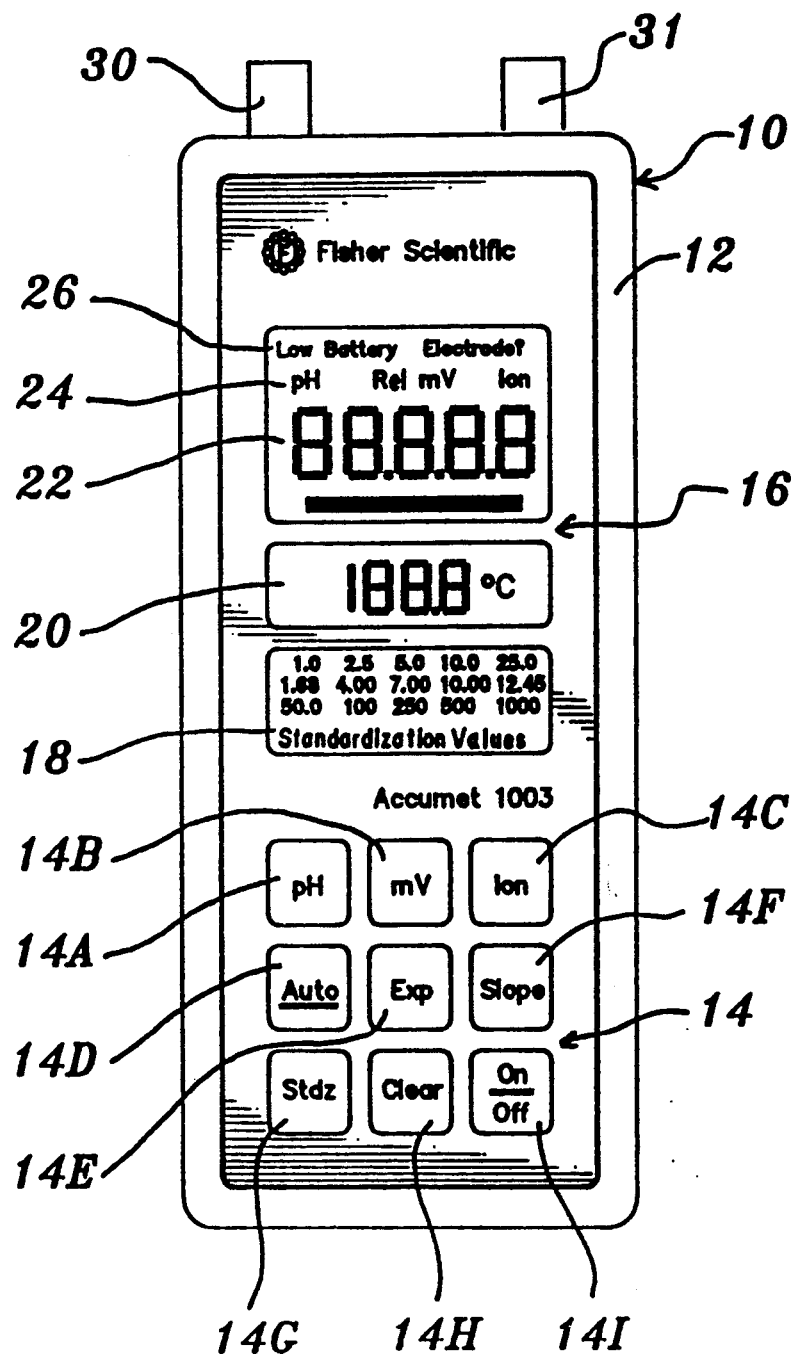
FIG. 1A is a front view of a meter according to an embodiment on the present invention, in a test mode in which all displays are activated.

FIG. 1A illustrates the front of a pH/pX meter 10 according to one embodiment of the present invention. The case 12 of meter 10 covers the exterior of the meter except for a panel containing keypad 14 and a series of display elements designated generally as 16. The keypad 14 includes nine keys 14A through 14I with indicia representing the function of each key as described below and in parent application U.S. Ser. No. 313,070 of Gibboney et al, filed Feb. 21, 1989, now U.S. Pat. No. 4,912,417. The display 16 includes, moving upward from the keypad 14, a standardization value display 18, a temperature display 20, a value display 22, a display for value type units 24 and a special message display 26. Two jacks 30 (for pH and mV) and 31 (for pX) extend upward through the top of case 12.

Figure 3A:
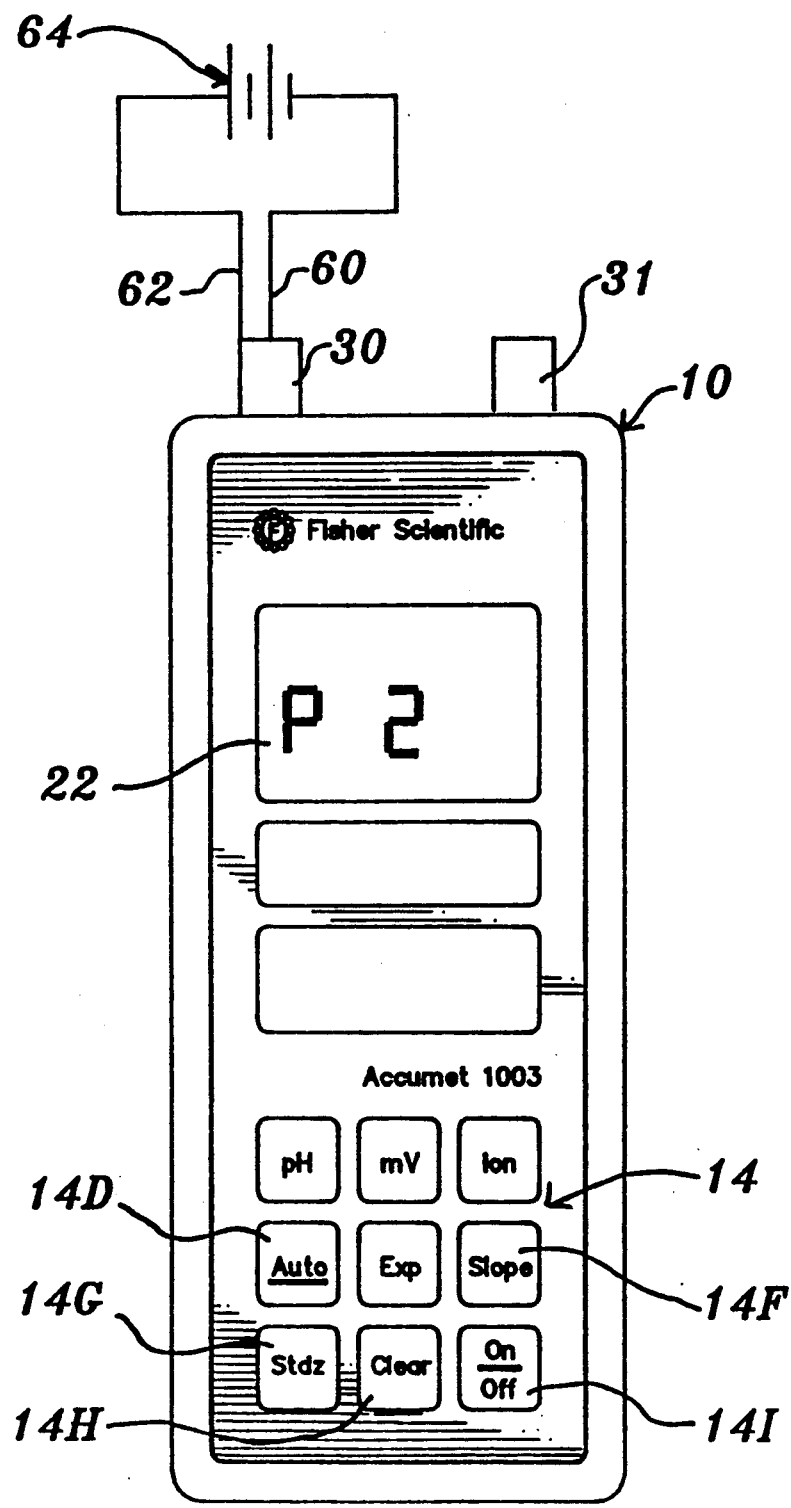
FIG. 3A is a front view of the meter of FIG. 1A connected to a schematically-shown first test circuit.
Figure 3B:
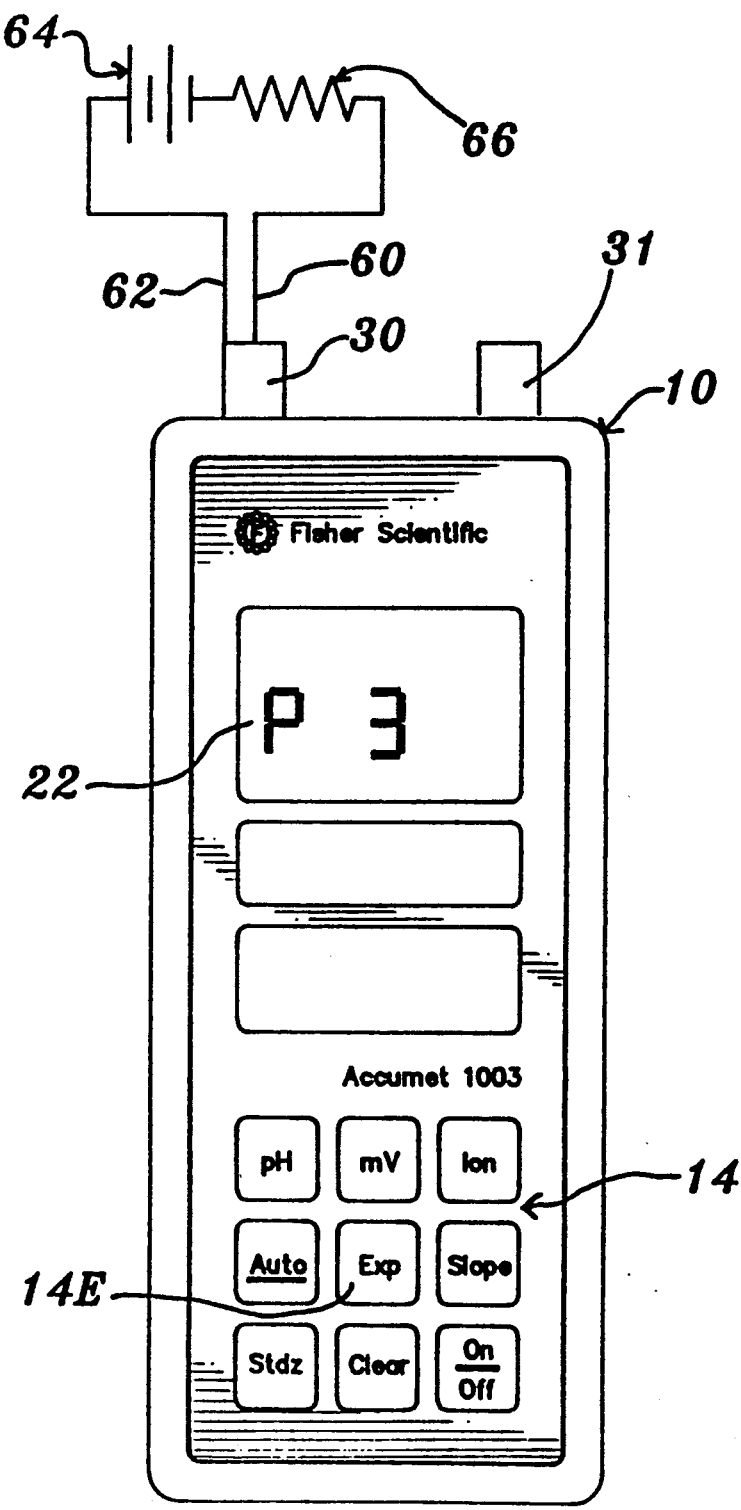
FIG. 3B is a front view of the meter of FIG. 1B connected to a schematically-shown second test circuit.
Figure 4:
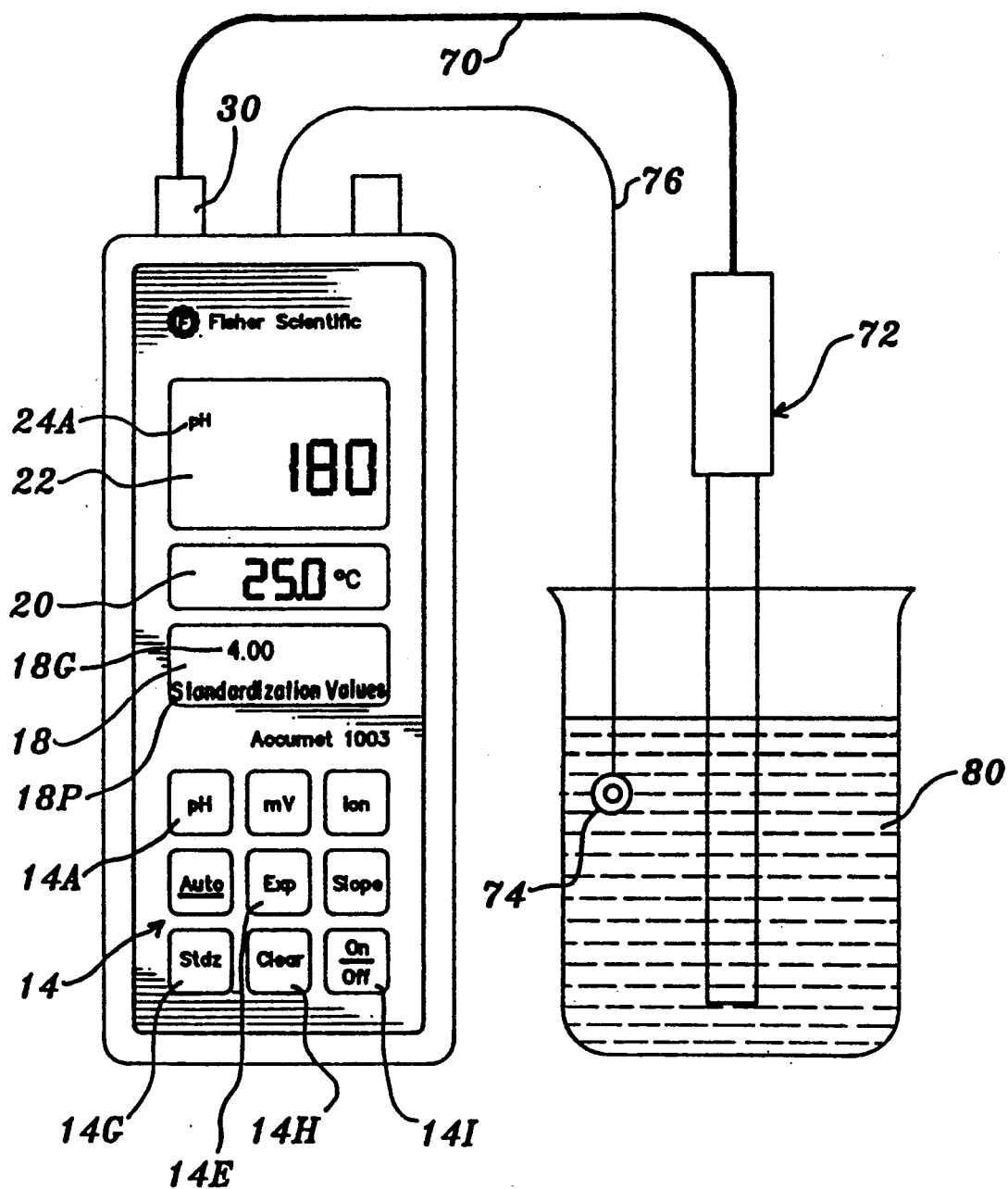
FIG. 4 is a front view of the meter of FIG. 1A connected to a combination pH/reference electrode and to a temperature probe, both immersed in a first standard solution.

The meter 10 is shown in FIG. 1A in a test mode in which all of the liquid crystal elements of display 16 (including all of display components 18, 20, 24 and 26) are activated. FIGS. 3A, 3B, and 4, below, indicate examples of the selective activation of various elements of the display 16.

Figure 1B:
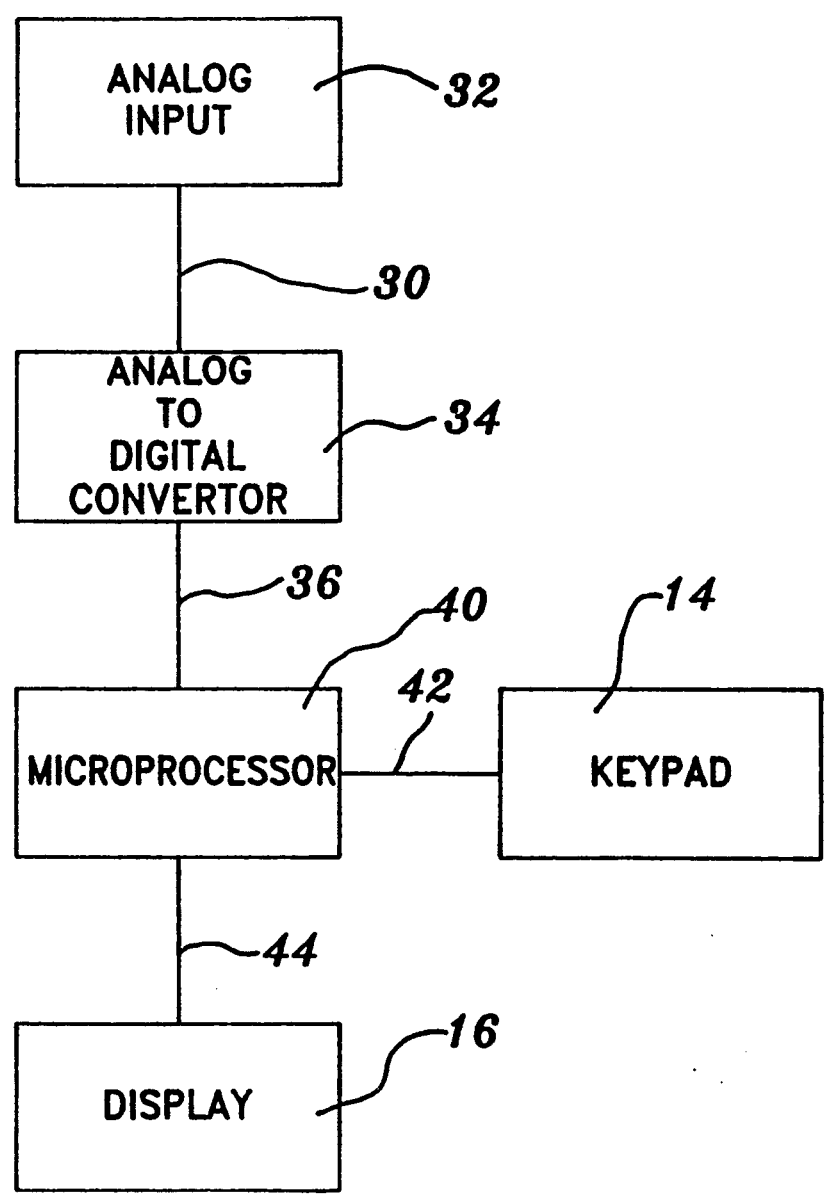
FIG. 1B is a schematic view of the major components of the meter of FIG. 1A connected to an analog input.

FIG. 1B is a schematic rendering of the functional components of meter 10. An analog input 32 (which as described below could be an electrode pair, a combination electrode or a test circuit) is connected via jack 30 to an analog to digital converter device 34, which converts the voltage of analog input 32 into a digital signal 36. That digital signal 36 is a first input into a microprocessor 40, described more fully below in reference to FIG. 1C and contained on a circuit board within case 12 of meter 10. Keypad input 42 represents the connection of the various keys of keypad 14 to microprocessor 40. Output 44 from microprocessor 40 to display 16 is representative of various control lines that connect microprocessor 40 to the individual liquid crystal display elements of the components of display 16.

FIG. 2 illustrates in schematic form the microprocessor 40, its major logic elements and the connecting elements. While microprocessor 40 could be constructed of an assembly of discrete logic devices or transistors, it is preferred to form microprocessor 40 as a custom mask microcomputer chip, such as the M50932-XXXFP chip from Mitsubishi Electric Corporation.

The two types of inputs to the microprocessor 40 are the digitized input 36 (shown as coming from A/D Converter 34 in FIG. 1B) and the keypad input 42 (shown as coming from keypad 14 in FIG. 1B). The two types of outputs from the microprocessor 40 are the display outputs to individual elements of display 16 and the channel selector output 46 which determines whether A/D Converter 34 (see FIG. 1B) is connected to jack 30 or to jack 31 or to the temperature jack between them (see FIG. 1A). FIG. 2 illustrates these two types of inputs and two types of outputs graphically above elements 16, 46, 36 and 42.

The two types of inputs and both types of outputs connect through the I/O interface 48 to the arithmetic logic unit 50 of microprocessor 40. Additional inputs to ALU 50 are timer circuits 52 used (for example) for indicating increments (such as each second) at which ALU performs certain functions. The microprocessor 40 also contains read only memory (ROM) 54 in which various program routines and constants are permanently stored and called up by ALU in a controlled fashion. Random access memory (RAM) 56 contains various values obtained by ALU 48 from I/O 48 or from computations on those values, on stored values already in RAM 56, on values from ROM 54 or on values from a variety of sources.

The operation of the components of the microprocessor 40 shown in FIG. 2 to perform various computations and routines will be described below after the description of the remaining figures. Additional description of the operation of microprocessor 40 during standardization and measurement of pH or of pX is contained in parent application U.S. Ser. No. 313,070, now U.S. Pat. No. 4,912,417.

FIG. 3A shows meter 10 connected to a first test circuit as part of the testing of the input current. A plug is inserted into jack 30 so that line 60 on the plug is connected to the inner contact of jack 30 and line 62 is connected to the outer contact or sleeve of jack 30. Lines 60 and 62 are connected to opposite poles of a battery 64 of known voltage E1, e.g., 0.475 V. The circuit represented by elements 60, 62 and 64 is of low impedance.

A person testing the meter in the configuration of FIG. 3A pushes, in order, buttons On/Off 14I, Stdz 14G, Clear 14H, Clear 14H and Slope 14F of keypad 14. Display 22 shows a message ("P2") at this point that indicates to the operator what test circuit to connect to jack 30 (if jack 31 is being tested, it is connected to a similar test circuit). The operator then connects jack 30 to circuit P2 and presses key 14D ("Auto") to initiate testing. The measured voltage for this circuit is then stored (as V1). The meter then indicates at display 22 the next circuit ("P3") to connect to jack 30 (and jack 31, if being tested). The meter 10 is then connected, as shown in FIG. 3B, to a circuit containing line 60, resistor 66 of high resistance (e.g., $5 \times 10^9$ ohms), battery 64 of known voltage E1 and line 62. By pushing the Exp key 14E of keypad 14 in this situation, the meter 10 measures the voltage drop between line 62 and line 60 in the circuit of FIG. 3B and stores that value in RAM 56 as V2. Technically, the meter actually measures the difference between the measured voltage drop between line 62 and line 60 in the circuit and the measured voltage when line 60 is shorted to line 60 ($V_{os}$), but it will be simpler to speak of the voltage drop between line 62 and line 60 as the measured value V2. V1 is now compared to V2, and the difference is compared to an acceptance limit (for example, 5 mV). If V2−V1 is 5 mV or less, the meter has an acceptable internal bias current (as described below) and passes. If V2−V1 is more than 5 mV, then the internal bias current (also sometimes called input current) exceeds specified levels and an error message ("ERR 7") would be displayed on display 22. If the Ion circuit were being tested (by having jack 32 so connected), then if the internal bias current exceeded the specified level, an error message ("Err 8") would be displayed at display 22. If both jacks were connected to test circuits, the meter would test one and then the other and display only that error message which was appropriate. If such bias current testing were part of quality control on a newly assembled meter 10, then either such error message would cause the meter 10 to fail. If such bias testing were part of the evaluation of a meter 10 after a period of use, such an error message would indicate a requirement for repair or replacement.

The selection of an acceptance criterion for V1−V2 is generally fixed in the design of a particular embodiment of the meter. The basis for such a selection is illustrated here. Let it be assumed that one wants meter 10 to have an accuracy of 0.1 mV (approximately 0.002 pH units for most pH electrodes). Then an allowable bias current would be $I = V/R = 10^{-4}$ volts/$10^8$ Ohms = $10^{-12}$ amps, since a typical pH electrode impedance is about $10^8$ ohms. In the circuit of FIG. 3B, the voltage drop across resistor 66 would correspond to V1−V2 and be:

$$V_{66} = I \times R_{66}$$

and at the maximum permitted level of $I = 10^{-12}$ amps that would be $10^{-12} \times 5 \times 10^9 = 5 \times 10^{-3}$ volts = 5 mV. In similar fashion, a permitted internal bias current of 5 * $10^{-12}$ amps would correspond to V1−V2 being 25 mV or less; a permitted internal bias current (input current) of 1 * $10^{-11}$ amps would correspond to V1−V2 being 50 mV or less.

It is preferred that the acceptance criterion (in mV for V1−V2) be stored in ROM so that the meter can do a simple comparison. It is less preferred that the meter calculate an actual internal bias current from V1 −V2. The value for $R_{66}$ should be fixed, and should be sufficiently larger than the resistance of any electrode pair that the meter will be used with to give values for V1−V2 much larger than the accuracy of the meter (50 times as great in the example, but preferably at least 10 times as great: e.g., at least $10^9$ ohms for resistor 66 if electrodes of up to $10^8$ ohms are expected).

The testing of the meter 10 for acceptably high internal impedance involves both the measurement of V2, as described above, and the measurement of V4 in a similar fashion, but with a different voltage applied by the external circuit. V1 and V3 are used to check the accuracy of the input circuit by comparing the V1 value to the expected value of E1 and V2 to the expected value of E2, to assure that the correct test circuits have been connected. Assume that the P2 circuit (shown in FIG. 3A) had a voltage for battery 64 of 0.475 V and that the P3 circuit (shown in FIG. 3B) had a voltage for battery 64 of 0.475 V and a resistance (impedance) of resistor 66 of $5 \times 10^9$ ohms. The next circuit P4 would resemble the first two, but have a different applied voltage. For example, as shown in FIG. 3C circuit P4 would have a battery 65 of known voltage E2 (−0.475 V) and high impedance. To simplify operations, it is preferable that the same resistor 66 (of impedance $10^8$ ohms) be part of circuit P2 and of circuit P4 (i.e., R1 = R2). If a value V3 is to be obtained for reasons discussed above, then circuit P3 would have a battery 65 of −0.475 V and low impedance.

In operation, the meter 10 would display "P3" at display 22 at the conclusion of the measurement of V2 if the calculated value of V1−V2 was within specifications as described above. The meter would also verify that V1 was close to (within 0.1 volt of, for example) E1. The operator would then connect jack 30 (or jacks 30 and 31) to circuit P3 having battery 65 and low impedance. The operator would then press key 14F (labeled slope). The meter 10 would store the sensed potential as V3 once it stabilized, compare V3 to the expected value E2 and (if V3 was within 0.1 volt of E2, for example) display "P4" at display 22. The operator would then connect jack 30 (or jacks 30 and 32) to circuit P5 having battery 65 of known voltage E2 and resistor 66 in series. The operator would then press key 14D (labeled "Auto") and the potential would be measured until a stabilized value V4 was obtained. Once the measured potential stabilized, the meter would calculate the quantity (V4−V2). It should be appreciated, however, that V4 and V2 could also be measured alone, or could also be measure with V1, but without V3. The actual formula for internal impedance of the meter, after certain simplifying assumptions, is:

$$Z = \frac{V_4 - V_2}{\frac{E_2 - V_4}{R_1} - \frac{E_1 - V_2}{R_1}}$$

where Z is the actual internal impedance, $E_1$ is the potential of battery 64 in circuits P2 and P3 and $E_2$ is the potential of battery 65 in circuits P4 and P5.

Since meter 10 will be tested with circuits of known potentials $E_1$ and $E_2$, these values can be stored as constants in the meter (in ROM 54). Thus, the formula for Z reduces to the formula:

$$Z_o(E_2-E_1)/(Z_o+R_1) \leq V_4-V_2$$

If the criterion for Z is at least $10^{12}$ ohms ($Z_o=10^{12}$ ohms), if $R_1$ remains $5 \times 10^9$ ohms, if $E_2= +0.475$ V and $E_1= -0.475$ V, then $$V_4-V_2 \geq -0.9453 \text{ volts.}$$

Note that this required difference between V4 and V2 is less than the actual difference between E1 and E2 (0.950 volts) by the factor:

$$Z_o/(Z_o+R_1).$$

If criterion for Z is at least $10^{13}$ ohms or $10^{14}$ ohms, then the factor increases from 0.995 to 0.9995 and then 0.99995, and the required value of V4−V2 from 0.9453 volt to 0.9495 volt and then to 0.94995 volt.

After the meter has been thoroughly checked (for conventional features such as mV accuracy, temperature accuracy, input offset voltage, keyboard functionality and display functionality, as well as bias current as described above), it can be activated for one of several measuring modes (pH, pX or mV) and then standardized (especially for pH or pX). FIGS. 4 is illustrative of an intermediate state in the standardization of meter 10 for pH with buffer for pH 4.00 (that value represents the pH of the buffer at 25 deg C.). Operation of the meter 10 with other standardization buffers and in the measurement of pH or pX values of samples is described in Application 313,070 of Gibboney et al, the disclosure of which is incorporated herein by reference.

Referring again to FIGS. 1A and 4, first the meter is turned on by pressing button 14I on keypad 14. The pH mode can then be selected by pressing button 14A. If there are any standardization values already stored, they can be cleared by pressing buttons 14G and 14H successively. Resolution of the display 22 can be adjusted with button 14E (in the pH mode between tenths, hundredths and thousandths of a pH unit; in the Ion mode between two and three significant figures). The location of the decimal in display 22 will indicate in the pH mode which resolution is selected; and the decimal will move between the three positions shown on display 22 in FIG. 1A with each press of key 14E ("EXP" for expansion).

A double cable 70 connects jack 30 with a combination pH/reference electrode 72 which is immersed in a first buffer solution 80. As is conventional, the reference portion of electrode 72 is connected by cable 70 to the exterior or sleeve of jack 30 and the working pH element of electrode 72 is connected by cable 70 to the interior contact of jack 30. Buffer 80 can be any of the NBS standard pH buffers (1.68, 4.00, 7.00, 10.00 or 12.45 at 25 deg C.), but will be illustrated as buffer 4.00.

A temperature probe 74 in buffer 80 is connected by cable 76 to a jack (not shown) extending through the top of housing 12 to the A/D input 36 within meter 10. The temperature sensed by temperature probe 74 is displayed by display 20 and used by ALU 50 in various computations. In general, ALU causes the temperature to be displayed as degrees Celsius, but uses the ratio of mV (at jack 30) divided by degrees Kelvin (at probe 74) for most calculations.

By pushing key 14G with the meter 10 in the pH mode (as indicated at 24A on display 22), the meter 10 takes the signal at jack 30 and searches which (of the five) standardization values it approximates (for the temperature shown at display 20 which is assumed in this example to be 25 deg C. or 298.16 deg K.). While this search is occurring, the words "Standardization Values" at 18P on display 18 flash. Once buffer 80 is recognized as a pH 4.00 buffer, that numeral at 18G on display 18 flashes (the words at 18P now remain displayed). While "4.00" is flashing at 18G, display 22 shows the actual voltage measured at jack 30 (this is the stage actually indicated in FIG. 4A, with 180 millivolts shown on display 22). Once meter 10 has sensed a stabilized value at jack 30 (by the averaging and checking technique described below), the "4.00" displayed at 18G remains on and the numerals "4.00" become displayed at display 22. That value can be displayed as "4.0", "4.00" or "4.000" depending upon the resolution selected with key 14E, which can be changed at any time. If the temperature were not 25 deg C., the value displayed at display 22 would be the pH of buffer 80 at that temperature (e.g., 4.06 at 50 deg C.).

Combination pH/reference electrode 72 can now be removed from buffer 80, as shown in FIG. 4, rinsed and placed in a second standard buffer (e.g., a pH 7.00 buffer) as described in parent application U.S. Ser. No. 313,070. The electrode 72 can then be rinsed and immersed in a sample solution of unknown pH as shown in FIG. 4C of parent U.S. Ser. No. 313,070. In such fashion, pH meter 10 can now be used to measure the pH of multiple samples using the stored standardization values for pH 4.00 and pH 7.00 (actually the stored values of mV/deg K for buffers 80 and 82). A third standardization value can be similarly obtained with a different buffer (1.68, 10.00 or 12.45) and, in conventional fashion, meter 10 will take the voltage of a subsequent sample, determine which two standards are appropriate and convert to pH units using the values for mV/deg K for those two standards and for the sample. If standardization is performed with a fourth buffer (e.g., 1.68) different from the three for which standardizations are stored (e.g., 4.00, 7.00 and 10.00), the furthest standardization (10.00) will be erased from RAM and the three new standardizations (1.68, 4.00 and 7.00) will be stored in RAM and indicated on display 18.

After measuring various samples, the standardizations of meter 10 can be updated by repeating the above procedure with any of the three buffers As described in parent application Ser. No. 313,070, now U.S. Pat. No. 4,912,417, microprocessor 40 will cause the other two stored standardization values to be adjusted based upon the change in the measured standardization value.

Returning, now, to the testing of meter 10 with control circuits, as illustrated in FIGS. 3A and 3B, the microprocessor 40 would receive the voltage difference between line 62 and line 60 (V1 measured as in FIG. 3A, V2 measured as in FIG. 3B) as an analog input 32 (see FIG. 1B) converted to a digitized input 36 by A/D Converter 34. The subroutine would cause the ALU 50 to measure and store V1 and measure and store V2. V1 and V2 values would be stored only if they have stabilized (on a running average basis to 0.1 mV) for five seconds.

Once values for V1 and V2 have been obtained, the ALU 50 would then compare V1 to V2 (calculate V1−V2) and compare V1−V2 to the acceptance criterion (e.g., 5 mV). If the criterion is not passed, the ALU 50 causes "Err 7" to be displayed at display 22 and the meter 10 is rejected (if quality control), or is designated for repair or replacement (if use or service testing). The exact duplicate of this procedure is then performed on the ion channel with the rejection message being "Err 8" on display 22. If the criteria for internal bias current have been met, then microprocessor 40 causes display 22 to display "P4".

The operation of microprocessor 40 to determine that V2 has stabilized is exemplified by the following table. The determination that each of V1, V3 and V4 has stabilized proceeds in a similar fashion.

| millivolts | Initial readings over 161 mV | | |
|---|---|---|---|
| | average | change | |
| 160.9 | 161.66 | 0.76 | |
| 160.7 | 161.3 | 0.6 | |
| 160.5 | 160.98 | 0.48 | |
| 160.3 | 160.72 | 0.42 | |
| 160.1 | 160.5 | 0.4 | |
| 159.9 | 160.3 | 0.4 | |
| 159.9 | 160.14 | 0.24 | |
| 159.8 | 160.0 | 0.2 | |
| 159.6 | 159.86 | 0.26 | |
| 159.6 | 159.76 | 0.16 | |
| 159.5 | 159.68 | 0.18 | |
| 159.5 | 159.68 | 0.18 | |
| 159.4 | 159.52 | 0.12 | |
| 159.4 | 159.48 | 0.08 | |
| 159.3 | 159.42 | 0.12 | |
| 159.3 | 159.38 | 0.08 | |
| 159.3 | 159.34 | 0.04 | |
| 159.3 | 159.32 | 0.02 | |
| 159.2 | 159.28 | 0.08 | |
| 159.3 | 159.28 | −0.02 | Acceptance of V2 |

-continued

| millivolts | Initial readings over 161 mV | |
|---|---|---|
| | average | change |
| 159.3 | 159.28 | −0.02 |
| 159.2 | 159.26 | 0.06 |
| 159.2 | 159.24 | 0.04 |
| 159.2 | 159.24 | 0.04 |
| 159.2 | 159.22 | 0.02 |

In the four circuits, the meter could measure and store in such fashion values of V1, V2, V3 and V4 of 159.3, 159.28, 587.2 and 586.94, respectively. The meter would calculate for V4−V2 the difference 427.66 mV. Using the above formula, the acceptance criterion would be at least 407.52 mV for an internal resistance of at least $10^{11}$ ohms or at least 425.77 mV for an internal resistance of at least $10^{12}$ ohms or at least 427.69 mV for an internal resistance of at least $10^{13}$ ohms. The actual internal resistance one could calculate from V4 and V2 is $8.9 \times 10^{12}$ (passing the first two specifications, but not the third one). Appropriately, 427.66 mV exceeds the first two criteria, but not the 427.69 mV criterion.

We claim:

1. A method for testing a pH or pX meter for low internal impedance which comprises the steps:
   a) connecting the electrode inputs of the meter to an external circuit having a known voltage E1 and a large known external resistance R1 and storing the measured voltage V2,
   b) connecting the electrode inputs of the meter to an external circuit having a known voltage of value E2 and the large known external resistance R1 and storing the measured voltage V4,
   c) having the meter calculate the value:

$$(V_4 - V_2)$$

and compare that calculated value to a permitted range which is preset in the meter and is based upon fixed values of E1, E2 and R1, and
   d) if that calculated value is outside preset limits, having the meter display an error message indicating that the meter is out of specification for internal impedance.

2. The method of claim 1 further comprising the step:
   a1) connecting the electrode inputs of the meter to an external circuit having the known voltage E1 and a low external resistance and storing the measured voltage V1, and wherein the meter also calculates (V1-V2) as a measurement of internal bias current.

3. The method of claim 2 wherein each of V1, V2 and V4 are stored for purposes of calculation only once a running average of the voltage values measured with the respective external circuit has equalled the latest measured voltage value for that external circuit for a fixed time period.

4. The method of claim 1 wherein each of V2 and V4 are stored for purposes of calculation only once a running average of the voltage values measured with the respective external circuit has equalled the latest measured voltage value for that external circuit for a fixed time period.

5. The method of claim 1 wherein the preset limit for (V4−V2) are based upon the formula $$Z_o(E_2-E_1)/(Z_o+R_1) \leq V_4 - V_2$$

wherein $Z_o$ is the minimum acceptable internal impedence of the pH or pX meter.

* * * * *